(12) United States Patent
Kushida

(10) Patent No.: US 9,427,146 B2
(45) Date of Patent: Aug. 30, 2016

(54) OPHTHALMOLOGIC APPARATUS

(71) Applicant: CANON KABUSHIKI KAISHA, Tokyo (JP)

(72) Inventor: Akihiro Kushida, Kawasaki (JP)

(73) Assignee: Canon Kabushiki Kaisha, Tokyo (JP)

( * ) Notice: Subject to any disclaimer, the term of this patent is extended or adjusted under 35 U.S.C. 154(b) by 0 days.

(21) Appl. No.: 14/520,182

(22) Filed: Oct. 21, 2014

(65) Prior Publication Data
US 2015/0116663 A1 Apr. 30, 2015

(30) Foreign Application Priority Data
Oct. 24, 2013 (JP) ................. 2013-221089

(51) Int. Cl.
*A61B 3/00* (2006.01)
*A61B 3/10* (2006.01)

(52) U.S. Cl.
CPC ............. *A61B 3/0041* (2013.01); *A61B 3/00* (2013.01); *A61B 3/0025* (2013.01); *A61B 3/0033* (2013.01); *A61B 3/102* (2013.01); *A61B 3/1025* (2013.01)

(58) Field of Classification Search
CPC .. A61B 3/0041; A61B 3/102; A61B 3/0025; A61B 3/0033; A61B 3/1025; A61B 3/00; A61B 3/0008; A61B 3/0066; A61B 3/10; A61B 3/12
USPC .................................. 351/205, 206
See application file for complete search history.

(56) References Cited

U.S. PATENT DOCUMENTS

| | | | | |
|---|---|---|---|---|
| 2005/0071193 A1* | 3/2005 | Kalies | ........... | G06F 19/326 705/2 |
| 2007/0258630 A1* | 11/2007 | Tobin | ........... | G06K 9/0061 382/128 |
| 2008/0137034 A1* | 6/2008 | Wernick | ........... | A61B 3/1216 351/221 |
| 2009/0111708 A1* | 4/2009 | Seddon | ........... | C12Q 1/6883 506/9 |
| 2011/0007957 A1* | 1/2011 | Sakagawa | ........... | A61B 3/102 382/131 |
| 2011/0275931 A1* | 11/2011 | Debuc | ........... | A61B 3/102 600/425 |

FOREIGN PATENT DOCUMENTS

| | | |
|---|---|---|
| JP | 2009089792 A | 4/2009 |
| JP | 2013153884 A | 8/2013 |
| WO | 2006022045 A1 | 3/2006 |

* cited by examiner

*Primary Examiner* — Bumsuk Won
*Assistant Examiner* — William R Alexander
(74) *Attorney, Agent, or Firm* — Canon U.S.A. Inc., IP Division

(57) ABSTRACT

An ophthalmologic apparatus includes an analyzing unit that analyzes a tomographic image, a comparison target selecting unit that selects a statistical information in the closest age-group if an age calculated from a birth date input to a patient information input unit is outside a range of the age-groups of the statistical information, and a comparison unit that compares a result of the analysis performed by the analyzing unit with the statistical information selected by the comparison target selecting unit.

12 Claims, 21 Drawing Sheets

FIG. 4

| PATIENT ID | A0005 | BIRTH DATE | 1980/10/03 | (YYYY/MM/DD) |

PATIENT NAME

SEX ○ MALE ● FEMALE ○ OTHERS

RACE ASIAN ▼

HISPANIC
WHITE
BLACK
ASIAN

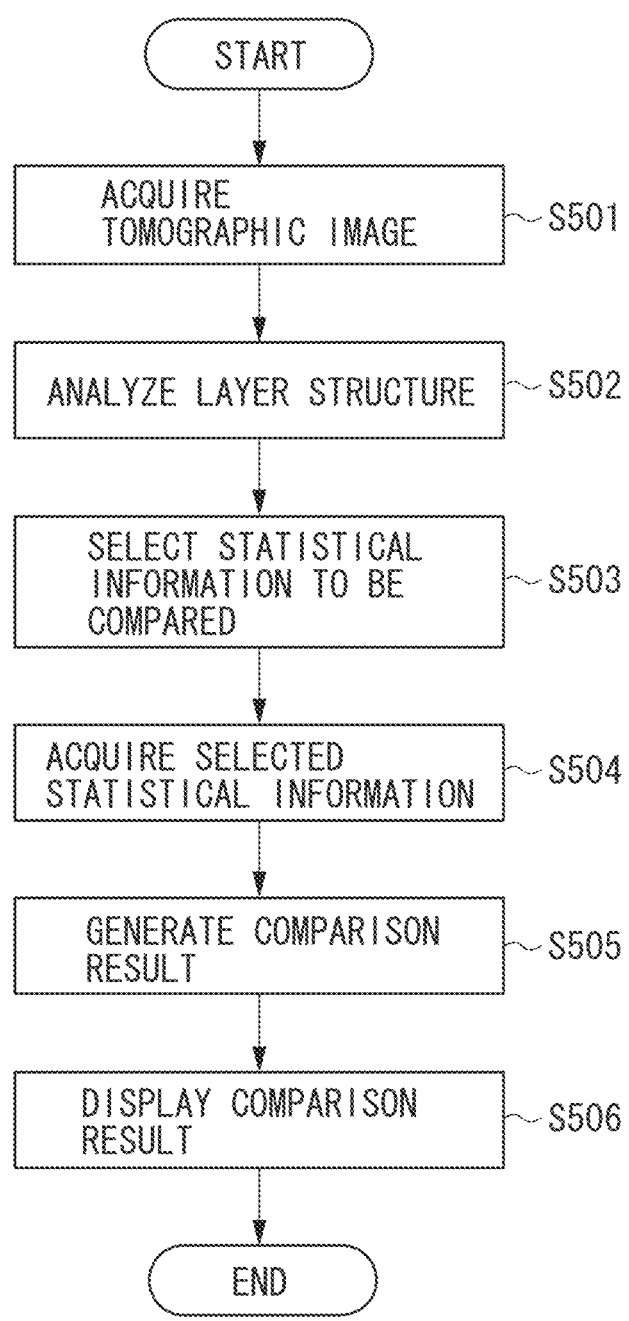

FIG. 6

| AGE-GROUP/RACE | HISPANIC | WHITE | BLACK | ASIAN |
|---|---|---|---|---|
| 18-30 | STATISTICAL INFORMATION A-1 | STATISTICAL INFORMATION B-1 | STATISTICAL INFORMATION C-1 | STATISTICAL INFORMATION D-1 |
| 31-40 | STATISTICAL INFORMATION A-2 | STATISTICAL INFORMATION B-2 | STATISTICAL INFORMATION C-2 | STATISTICAL INFORMATION D-2 |
| 41-50 | STATISTICAL INFORMATION A-3 | STATISTICAL INFORMATION B-3 | STATISTICAL INFORMATION C-3 | STATISTICAL INFORMATION D-3 |
| 51-60 | STATISTICAL INFORMATION A-4 | STATISTICAL INFORMATION B-4 | STATISTICAL INFORMATION C-4 | STATISTICAL INFORMATION D-4 |
| 61-70 | STATISTICAL INFORMATION A-5 | STATISTICAL INFORMATION B-5 | STATISTICAL INFORMATION C-5 | STATISTICAL INFORMATION D-5 |
| 71-85 | NO STATISTICAL INFORMATION | STATISTICAL INFORMATION B-6 | NO STATISTICAL INFORMATION | NO STATISTICAL INFORMATION |

FIG. 9

| INPUT RACE | RACE OF STATISTICAL INFORMATION TO BE COMPARED |
|---|---|
| JAPANESE | ASIAN |
| KOREAN | ASIAN |
| CHINESE | ASIAN |
| JAPANESE-WHITE | ASIAN, WHITE |
| JAPANESE-BLACK | ASIAN, BLACK |
|  | ASIAN, WHITE, BLACK, HISPANIC |

FIG. 13

| PARAMETER | RIGHT EYE | LEFT EYE |
|---|---|---|
| Disc Area (mm²) | 2.27 | 1.78 |
| Cup Volume (mm³) | 0.11 | 0.12 |
| C/D Area | 0.33 | 0.49 |
| C/D Vertical | 0.50 | 0.63 |
| C/D Horizontal | 0.64 | 0.82 |

FIG. 16

| PATIENT ID | A0005 | | BIRTH DATE/SEX | 1970/10/04 | MALE |
| PATIENT NAME | | | RACE | ASIAN | |

FIG. 17

| PATIENT ID | A0005 | BIRTH DATE/SEX | 1970/10/04 | MALE |
| PATIENT NAME | | RACE | (ASIAN) | |

OPHTHALMOLOGIC APPARATUS

BACKGROUND

1. Field of the Invention

Aspects of the present invention generally relate to an ophthalmologic apparatus.

2. Description of the Related Art

Various ophthalmologic apparatuses employing an optical device are used. Examples of an optical device for observing eyes include an anterior eye imaging device, a fundus camera, a scanning laser ophthalmoscope (SLO), and other various devices. Among these devices, an optical coherence tomography (OCT) imaging apparatus using optical coherence tomography utilizing multi-wavelength light wave interference can capture high-resolution tomographic images of a sample object. Hereinafter, the optical coherence tomography imaging apparatus will be referred to as an OCT apparatus. The OCT apparatuses are widely used in ophthalmologic diagnosis and the like to capture tomographic images of a retina in a fundus of a subject eye and also tomographic images of an anterior eye such as a cornea.

Meanwhile, it is known that a retina of a human eye includes plurality of layers. In ophthalmologic diagnosis, a doctor reads a layer structure and checks the state of a lesion area in a captured tomographic image. To check the state of a lesion area in a tomographic image of a retina, it is effective to display not only the tomographic image but also a layer thickness graph and a layer thickness map obtained by analyzing an image of a layer structure of the retina. It is also effective to detect an optic disc cup (Cup), an optic disc (Disc), and the like, and display measurement results such as sizes, ratios, and the like of the Cup, the Disc, and the like. It is also effective for checking a state of the lesion area to compare a calculated layer thickness, the sizes and ratios of the Cup, Disc, and the like with data of healthy eyes (international publication WO 2006/022045, Japanese Patent Application Laid-Open No. 2009-89792).

Statistical information in healthy eyes such as the thickness of each retinal layer, sizes, ratios, and distributions of the Cup, the Disc, and the like is stored in a normal database created for each race and each age-group from imaging data of healthy eyes (Japanese Patent Application Laid-Open No. 2013-153884).

In a case where imaging data of a patient is compared with statistical information stored in the normal database, the imaging data is compared with the statistical information in a race and an age-group that correspond to the race and age of the patient. An issue is how the imaging data of a patient should be compared with the statistical information stored in the normal database when a race or an age of the patient is outside a range of races or age-groups included in the statistical information.

International publication WO 2006/022045 and Japanese Patent Application Laid-Open Nos. 2009-89792 and 2013-153884 are silent about a method for the comparison of imaging data of a patient outside a range of races or age-groups included in statistical information stored in normal database.

SUMMARY OF THE INVENTION

Aspects of the present invention are generally directed to a technique capable of performing appropriate comparison of imaging data of a patient outside a range of races or age-groups included in statistical information stored in a normal database.

According to an aspect of the present invention, an ophthalmologic apparatus includes a tomographic image capturing unit configured to illuminate a subject eye with measurement light to capture a tomographic image, an analyzing unit configured to analyze the tomographic image captured by the tomographic image capturing unit, a patient information input unit configured to input a birth date as patient information, a statistical information storage unit configured to store statistical information created for each age-group from imaging data of plurality of healthy eyes, a statistical information acquisition unit configured to acquire the statistical information from the statistical information storage unit, a comparison target selecting unit configured to select the statistical information in the closest age-group in a case where an age calculated from the birth date input to the patient information input unit is outside a range of the age-groups of the statistical information, and a comparison unit configured to compare a result of the analysis performed by the analyzing unit with the statistical information selected by the comparison target selecting unit.

Further features of the present disclosure will become apparent from the following description of exemplary embodiments with reference to the attached drawings.

BRIEF DESCRIPTION OF THE DRAWINGS

FIG. 4 illustrates an example of a patient information input screen.

FIG. 5 is a flow chart according to an exemplary embodiment.

FIG. 6 illustrates an example of a normal database containing statistical information for each race and each age-group.

FIG. 9 illustrates a setting example in which a race of statistical information to be compared is set for each input race.

FIG. 13 illustrates an example of a displayed result of a comparison of measured values with statistical information in a normal database.

FIG. 16 illustrates a display example of normal patient information.

FIG. 17 illustrates a display example of patient information in a case of a comparison with a default race.

DESCRIPTION OF THE EMBODIMENTS

Details of an exemplary embodiment will be described.
<Configuration of Main Body>

Figure 1:
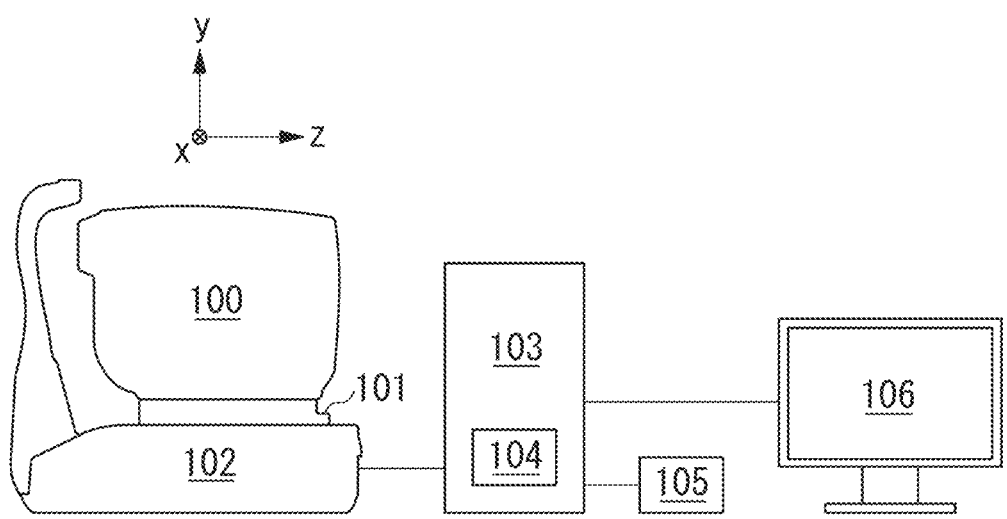
FIG. 1 illustrates an overall configuration according to an exemplary embodiment.

FIG. 1 is a side view of an OCT apparatus (ophthalmologic apparatus) according to the present exemplary embodiment.

An optical measurement system 100 is configured to capture an anterior eye image, an SLO fundus image of a subject eye, and a tomographic image. A stage unit 101 is capable of moving the optical measurement system 100 in XYZ-directions using a motor (not illustrated). A base unit 102 includes a built-in spectroscope described below.

A personal computer 103 controls the stage unit 101, controls alignment operations, arranges tomographic images, and the like. A storage unit 104 stores a program for tomographic imaging, patient information, imaging data, statistical information in a normal database, and the like. In other words, the storage unit 104 is an example of a statistical information storage unit.

An input unit 105 is used to give instructions to the personal computer 103. Specifically, the input unit 105 includes a keyboard and a mouse. A display unit 106 is a monitor or the like.
<Configurations of Optical Measurement System and Spectroscope>

Figure 2:
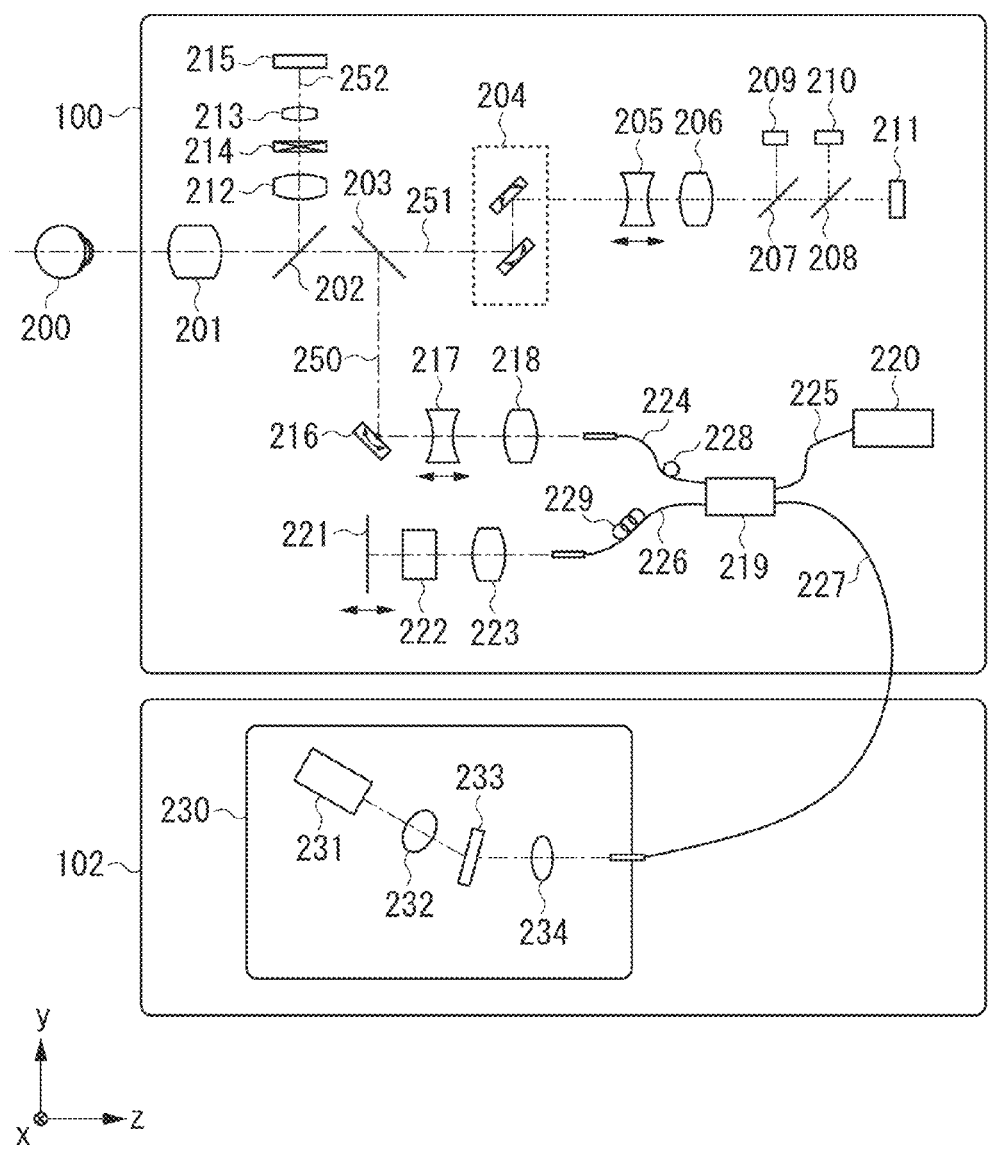
FIG. 2 illustrates an optical measurement system according to an exemplary embodiment.

The configurations of the optical measurement system 100 and the spectroscope will be described according to the present exemplary embodiment, with reference to FIG. 2.

First, an interior part of the optical measurement system 100 will be described. An objective lens 201 is disposed to face a subject eye 200, and a first dichroic mirror 202 and a second dichroic mirror 203 are disposed on an optical axis of the subject eye 200 and the objective lens 201. The first and second dichroic mirrors 202 and 203 cause light to separate into optical paths 250, 251, and 252 according to wavelength bands. The optical path 250 is for an OCT optical system. The optical path 251 is for an SLO optical system, which is for observing the subject eye 200 and capturing SLO fundus images, and the fixation lamp. The optical path 252 is for observing an anterior eye.

The optical path 251 for the SLO optical system and the fixation lamp includes an SLO scanning unit 204, lenses 205 and 206, a mirror 207, a third dichroic mirror 208, a photodiode 209, an SLO light source 210, and a fixation lamp 211.

The mirror 207 is a prism on which a perforated mirror or a hollow mirror is deposited. The mirror 207 separates illumination light emitted from the SLO light source 210 and return light from the subject eye 200. The third dichroic mirror 208 causes light to separate into optical paths for the SLO light source 210 and the fixation lamp 211 according to wavelength bands.

The SLO scanning unit 204 scans the subject eye 200 with light emitted from the SLO light source 210 and the fixation lamp 211. The SLO scanning unit 204 includes an X-scanner for perform scanning in an X-direction and a Y-scanner for perform scanning in a Y-direction. In the present exemplary embodiment, since the X-scanner is required to perform high-speed scanning, the X-scanner includes a polygon mirror, and the Y-scanner includes a galvanometer mirror.

The lens 205 is driven by a motor (not illustrated) to focus the SLO optical system and the fixation lamp. The SLO light source 210 emits light having a wavelength of around 780 nm. The photodiode 209 detects return light from the subject eye 200. The fixation lamp 211 emits visible light to facilitate visual fixation of the subject.

Light emitted from the SLO light source 210 is reflected by the third dichroic mirror 208, passes through the mirror 207 and the lenses 206 and 205, and is scanned over the subject eye 200 by the SLO scanning unit 204. Return light from the subject eye 200 returns through the same path as that of the projection light is then reflected by the mirror 207 to be guided to the photodiode 209, whereby an SLO fundus image is acquired.

Light emitted from the fixation lamp 211 passes through the third dichroic mirror 208, the mirror 207, and the lenses 206 and 205, and is then scanned over the subject eye 200 by the SLO scanning unit 204. At this time, the fixation lamp 211 is blinked in synchronization with the movement of the SLO scanning unit 204, whereby an arbitrary shape is formed at an arbitrary position on the subject eye 200 to facilitate visual fixation of the subject.

On the optical path 252 for the observation of an anterior eye, lenses 212 and 213, a splitting prism 214, and a charge-coupled device (CCD) sensor 215 for the observation of an anterior eye are disposed. The CCD sensor 215 is configured to detect infrared light and has sensitivity at a wavelength of the illumination light (not illustrated) for the observation of an anterior eye, specifically near 970 nm. The splitting prism 214 is disposed at a position conjugate with the pupil of the subject eye 200, and the distance of the optical measurement system 100 in the Z-direction (anteroposterior direction) from the subject eye 200 can be detected as a split image of the anterior eye.

As described above, the optical path 250 of the OCT optical system is configured to capture a tomographic image of the subject eye 200. More specifically, the optical path 250 is configured to acquire interference signals for forming a tomographic image. An XY scanner 216 is for scanning the subject eye 200 with light. Although the XY scanner 216 is illustrated as a single mirror, the XY scanner 216 is a galvanometer mirror configured to perform scanning in two axial directions, i.e., X- and Y-directions.

There is also provided lenses 217 and 218. The lens 217 is driven by a motor (not illustrated) to cause light emitted from the OCT light source 220 and output from the fiber 224 connected to the optical coupler 219 to focus on the subject eye 200. This focus adjustment causes the return light from the subject eye 200 to simultaneously form a spot on a leading end of the fiber 224 and enter the fiber 224.

Next, an optical path from the OCT light source 220 and the configurations of a reference optical system and the spectroscope, will be described. The OCT light source 220, a reference mirror 221, a dispersion compensation glass 222, a lens 223, an optical coupler 219, single-mode optical fibers 224 to 227 connected to the optical coupler 219 and integrated, and a spectroscope 230 are disposed therein.

The foregoing configuration forms a Michelson interference system. Light emitted from the OCT light source 220 passes through the optical fiber 225 and is then split via the optical coupler 219 into measurement light toward the optical fiber 224 and reference light toward the optical fiber 226. The measurement light passes through the optical path of the OCT optical system described above, illuminates the subject eye 200, which is an observation target, is reflected or scattered by the subject eye to return through the same optical path, and then arrives at the optical coupler 219.

On the other hand, the reference light passes through the optical fiber 226, the lens 223, and the dispersion compensation glass 222, arrives at the reference mirror 221, and is reflected. The dispersion compensation glass 222 is inserted to balance the dispersion of the measurement light and the dispersion of the reference light. Then, the reflected light returns through the same optical path to reach the optical coupler 219.

The optical coupler 219 combines the measurement light and the reference light together to form interference light. Interference occurs when the optical path lengths of the measurement light and the reference light become substantially equal. The reference mirror 221 is held in such a manner that the reference mirror 221 can be adjusted in the optical axis direction by a motor (not illustrated) and a driving mechanism (not illustrated) to equalize the optical path length of the reference light with the optical path length of the measurement light, which varies depending on the subject eye 200. The interference light is guided to the spectroscope 230 via the optical fiber 227.

A polarization adjustment unit 228 for the measurement light is provided in the optical fiber 224. A polarization adjustment unit 229 for the reference light is provided in the optical fiber 226. The polarization adjustment units 228 and 229 include several looped portions formed by pulling around the respective optical fibers. The loop-shaped portions are rotated about the longitudinal direction of the respective fibers to apply torsion to the fibers, whereby each of the polarization states of the measurement light and the reference light can be adjusted to each other.

The spectroscope 230 includes lenses 232 and 234, a grating 233, and a line sensor 231. The interference light output from the optical fiber 227 passes through the lens 234 to become parallel light. Then, the parallel light is dispersed by the grating 233 and then focused onto the line sensor 231 by the lens 232.

Next, a portion around the OCT light source 220 will be described. The OCT light source 220 is a super luminescent diode (SLD), which is a typical low coherent light source. The center wavelength is 855 nm, and the wavelength band width is about 100 nm. The band width is an important parameter, because it affects the resolution of an acquired tomographic image in the optical axis direction.

As to the type of the light source, while the SLD is selected in the present exemplary embodiment, any other light sources capable of emitting low coherent light such as amplified spontaneous emission (ASE) can be used. Since the object to be measured is an eye, the center wavelength is desirably near-infrared light. Desirably, the center wavelength is as short as possible, because the center wavelength affects the resolution of an acquired tomographic image in the horizontal direction. For the above-described reasons, the center wavelength is set to 855 nm.

While the present exemplary embodiment employs the Michelson interferometer as the interferometer, a Mach-Zehnder interferometer may also be used. Desirably, a Mach-Zehnder interferometer is used if the difference between the amount of measurement light and the amount of reference light is large, and a Michelson interferometer is used if the difference is small.

The above-described configuration enables capturing of a tomographic image of the subject eye and also capturing of an SLO fundus image of the subject eye with high contrast even when the light is near-infrared light.

<Tomographic Image Capturing Method>

Next, a method for capturing a tomographic image by use of an OCT apparatus will be described.

The OCT apparatus controls the XY scanner 216 to capture a tomographic image of a predetermined site of the subject eye 200. A trajectory of scanning tomographic image acquisition light in the subject eye is referred to as a scan pattern. Examples of a scan pattern include cross scanning in which light is scanned vertically and horizontally to cross at a single point, three-dimensional (3D) scanning in which light is scanned to fill in an entire area to acquire a three-dimensional tomographic image, and the like. In a case where detailed observation of a specific site is desired, the cross scanning is suitable. In a case where observation of the layer structure or the layer thickness of an entire retina is desired, the 3D scanning is suitable.

In the present exemplary embodiment, an imaging method in which the 3D scanning is executed will be described. First, the measurement light is scanned in the X-direction specified in FIG. 2, and the line sensor 231 captures information about a predetermined number of imaging lines from an imaging area of the subject eye along the X-direction. A luminance distribution on the line sensor 231 obtained at a position in the X-direction is subjected to fast Fourier transform (FFT) to obtain a linear luminance distribution, and the linear luminance distribution is converted into density information to be displayed on the monitor 106. The density information is referred to as an A-scan image.

A two-dimensional image in which the plurality of A-scan images is arranged is referred to as a B-scan image. After the plurality of A-scan images for forming a single B-scan image are captured, the scan position in the Y-direction is shifted, and then the scanning along the X-direction is performed again, whereby a plurality of B-scan images are acquired.

The monitor 106 displays the plurality of B-scan images or a three-dimensional tomographic image formed from the plurality of B-scan images so that the examiner can diagnose the subject eye. While the example in which the plurality of B-scan images in the X-direction is captured to obtain a three-dimensional tomographic image is described, a plurality of B-scan images in the Y-direction may be captured to obtain a three-dimensional tomographic image.

<Function Block Diagram>

Figure 3:
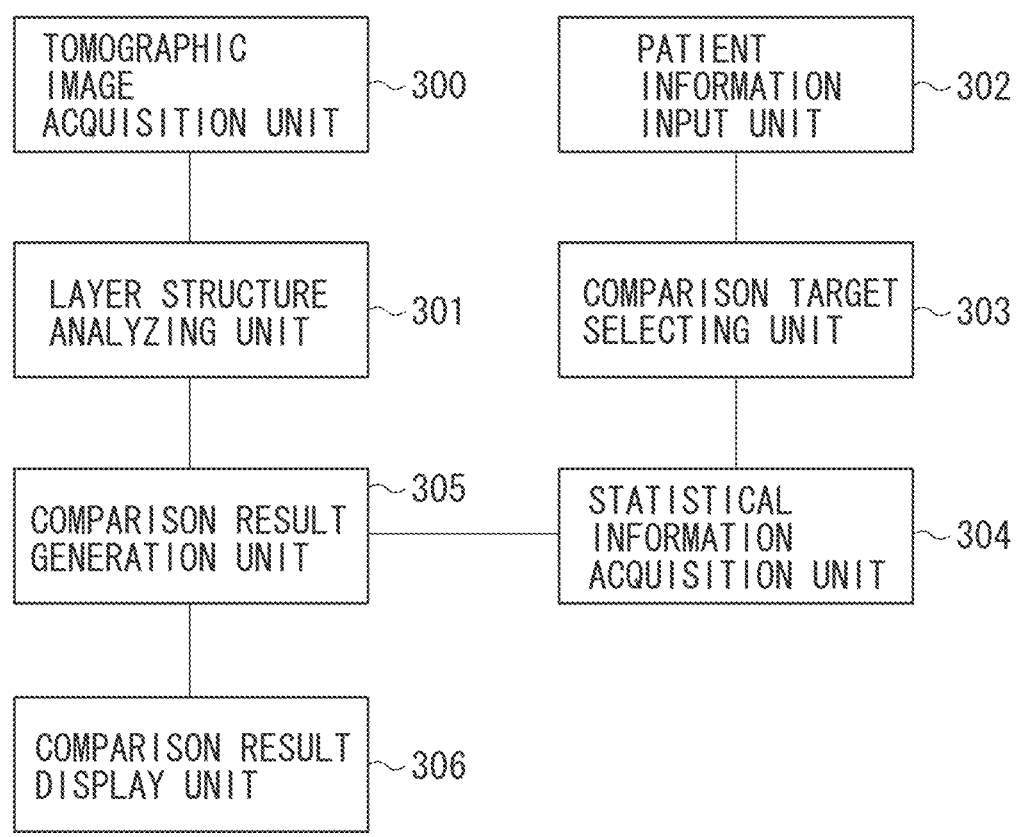
FIG. 3 is a function block diagram according to an exemplary embodiment.

FIG. 3 is a function block diagram according to the present exemplary embodiment.

A tomographic image acquisition unit 300 acquires a tomographic image from data captured by the line sensor 231.

A layer structure analyzing unit 301 analyzes the tomographic image acquired by the tomographic image acquisition unit 300 to discriminate the layer structure, the Cup, the Disc, and the like.

To a patient information input unit 302, patient information such as a patient identification (ID), patient name, birth date, sex, and race can be input trough the input unit 105 via a patient information input screen illustrated in FIG. 4.

A comparison target selecting unit 303 selects statistical information in the normal database with which imaging data of the patient is to be compared, based on the race input to the patient information input unit 302 and an age calculated from the birth date.

A statistical information acquisition unit 304 acquires from the storage unit 104 the statistical information selected by the comparison target selecting unit 303.

A comparison result generation unit 305 generates a comparison result from the information analyzed by the layer structure analyzing unit 301, such as the layer structure, the Cup, and the Disc, and the statistical information in the normal database that is acquired by the statistical information acquisition unit 304.

A comparison result display unit 306 displays on the monitor 106 the comparison result generated by the comparison result generation unit 305, together with the SLO fundus image, the tomographic image, and the like.

<Flow Chart>

FIG. 5 is a flow chart according to the present exemplary embodiment.

In step S501, the tomographic image acquisition unit 300 acquires a tomographic image from data captured by the line sensor 231.

In step S502, the layer structure analyzing unit 301 analyzes the tomographic image acquired by the tomographic image acquisition unit 300 to discriminate the layer structure, the Cup, the Disc, and the like. The analysis of the layer structure uses differences in signal intensity due to different reflectances of the respective layers, whereby each layer can be discriminated.

In step S503, the comparison target selecting unit 303 selects statistical information in the normal database with which imaging data of the patient is to be compared, based on a race input to the patient information input unit 302 and an age calculated from a birth date input to the patient information input unit 302.

In step S504, the statistical information acquisition unit 304 acquires from the storage unit 104 the statistical information selected by the comparison target selecting unit 303.

In step S505, the comparison result generation unit 305 generates a comparison result from the information analyzed by the layer structure analyzing unit 301, such as the layer structure, the Cup, and the Disc, and the statistical information in the normal database acquired by the statistical information acquisition unit 304.

In step S506, the comparison result display unit 306 displays on the monitor 106 the comparison result generated by the comparison result generation unit 305, together with the SLO fundus image, the tomographic image, and the like.

<Statistical Information in Normal Database>

As illustrated in FIG. 6, the normal database stores statistical information for each race and each age-group, including the layer thickness of each retinal layer, the sizes and ratios of the Cup, the Disc, distributions of the Cup, the Disc, and the like in healthy eyes. Age-groups for which statistical information is available may differ depending on the race. In the example illustrated in FIG. 6, only the race "White" has statistical information for the age-group of 71 to 85.

<Comparison Target Selection>

The selection of a comparison target, which is a feature of the present exemplary embodiment, will be described with reference to a flow chart illustrated in FIG. 7.

In step S700, whether the race of the patient corresponds to a race of the statistical information is determined. In a case where the race of the patient is not input, it is determined that the race of the patient does not correspond to a race of the statistical information. If the race of the patient does not correspond to a race of the statistical information (NO in step S700), the processing proceeds to step S701. If the race of the patient corresponds to a race of the statistical information (YES in step S700), the processing proceeds to step S702.

In step S701, the process ends without selecting statistical information.

In step S702, whether a birth date of the patient is input is determined. If the birth date of the patient is not input (NO in step S702), the processing proceeds to step S701, because an age of the patient is unknown. If the birth date of the patient is input (YES in step S702), the processing proceeds to step S703.

In step S703, whether the age of the patient is within a range of the age-groups of the statistical information in the corresponding race determined in step S700 is determined. If the age of the patient is within the range (YES in step S703), the processing proceeds to step S704. If the age of the patient is outside the range (NO in step S703), the processing proceeds to step S705.

In step S704, the statistical information in the race and age-group that correspond to the race and age of the patient is selected from the normal database. For example, if the race of the patient is Asian and the age of the patient is 35, statistical information D-2 is selected from the normal database illustrated in FIG. 6.

In step S705, statistical information in the closest age-group of the corresponding race is selected, because the normal database does not store statistical information in the race and age-group that correspond to the race and the age of the patient. For example, if the race of the patient is Asian and the age of the patient is 75, statistical information D-5 is selected. If the race of the patient is Asian and the age of the patient is 15, statistical information D-1 is selected.

<Comparison Target Selection Derivative Form 1>

Figure 8:
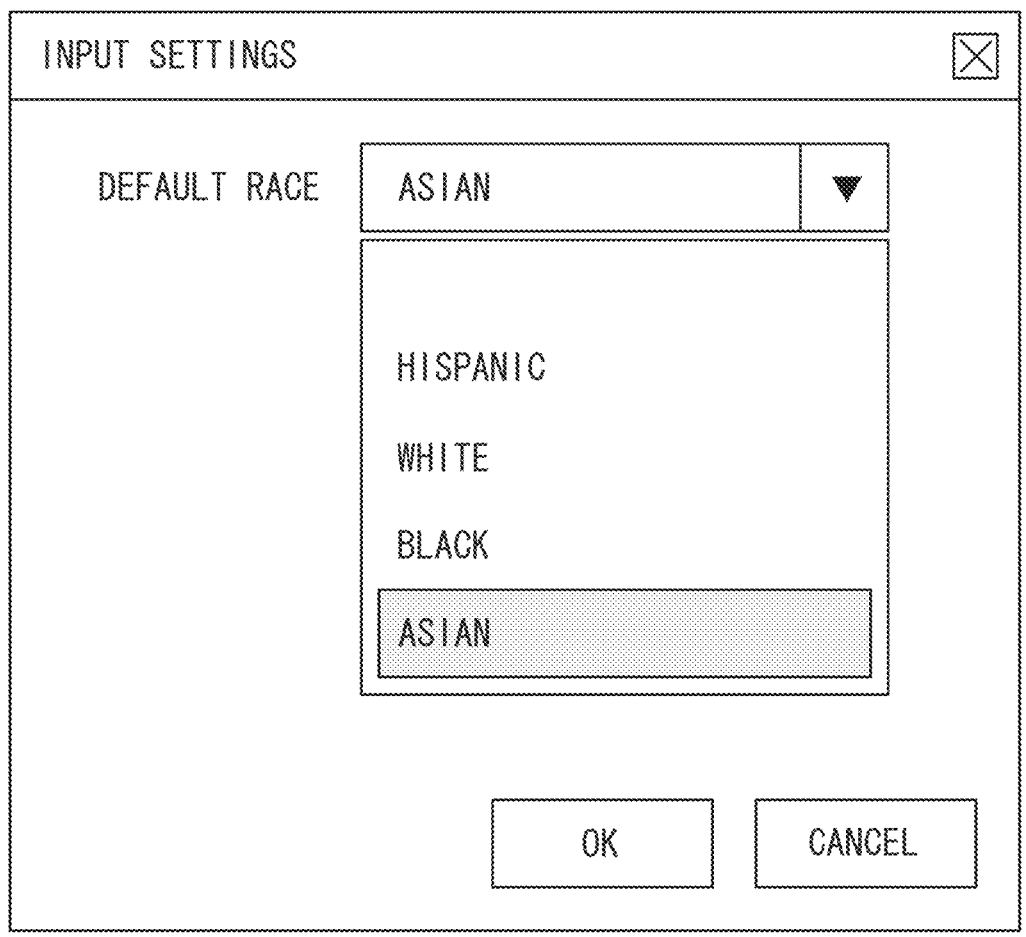
FIG. 8 illustrates an example of a default race setting screen.

A default race is preset via a setting input screen illustrated in FIG. 8. The default race setting is performed via the setting input screen. In this case, whether the default race corresponds to a race of the statistical information may be determined in step S700 if the race of the patient is not input. In a case where the majority of patients are of the same race and very few patients are of different races, setting the default race enables omission of the input of the races of most of the patients.

<Comparison Target Selection Derivative Form 2>

While FIG. 4 illustrates the patient input screen in which a race is selected from the list of races of the statistical information, there may be a case where a race is input in a form different from those of the races of the statistical information. For example, the race of an Asian patient may be input as Japanese, Korean, or Chinese. Further, the race of a patient may be input as Japanese-White, Japanese-Black, or the like. In these cases, as illustrated in FIG. 9, a race of the statistical information to be compared is preset according to the input race information. A plurality of races of the statistical information to be compared may be set. For example, if the patient is Japanese-White, the races "Asian" and "White" are set as comparison targets. Further, while a default race is set in Comparison target selection derivative form 1 if the race of the patient is not input, a plurality of races may be set as comparison targets, as shown in the lowermost section of the table illustrated in FIG. 9, in the case where the race of the patient is not input. In the case where no race is input, all races may be set as a comparison target. In a case where the race is input in a form that is not registered in the table illustrated in FIG. 9, either no races may be set as a comparison target, or all races may be set as a comparison target.

In a case where a plurality of races of statistical information is selected as comparison targets, whether the age of the patient is within the range of the age-groups of the statistical information is determined in step S703 for each of the plurality of races of the statistical information. For example, if the age of the patient is 75 and two races "White" and "Asian" of the statistical information in the normal database illustrated in FIG. 6 are selected as comparison targets, statistical information B-6 is selected for the race "White", whereas statistical information in the closest age-group, which is statistical information D-5, is selected for the race "Asian".

<Comparison Target Selection Derivative Form 3>.

In a case where race information about parents and grandparents of the patient is available, statistical information in a race that corresponds to the race of any one of the parents and grandparents may be set as a comparison target.

<Comparison Target Selection Derivative Form 4>

In the case where the age of the patient is outside the range of the age-groups of the statistical information, the statistical information in each age-group of the normal database may be plotted on a graph, and statistical information for the age of the patient may be estimated by curve approximation and then compared.

<Comparison Target Selection Derivative Form 5>

Figure 7:
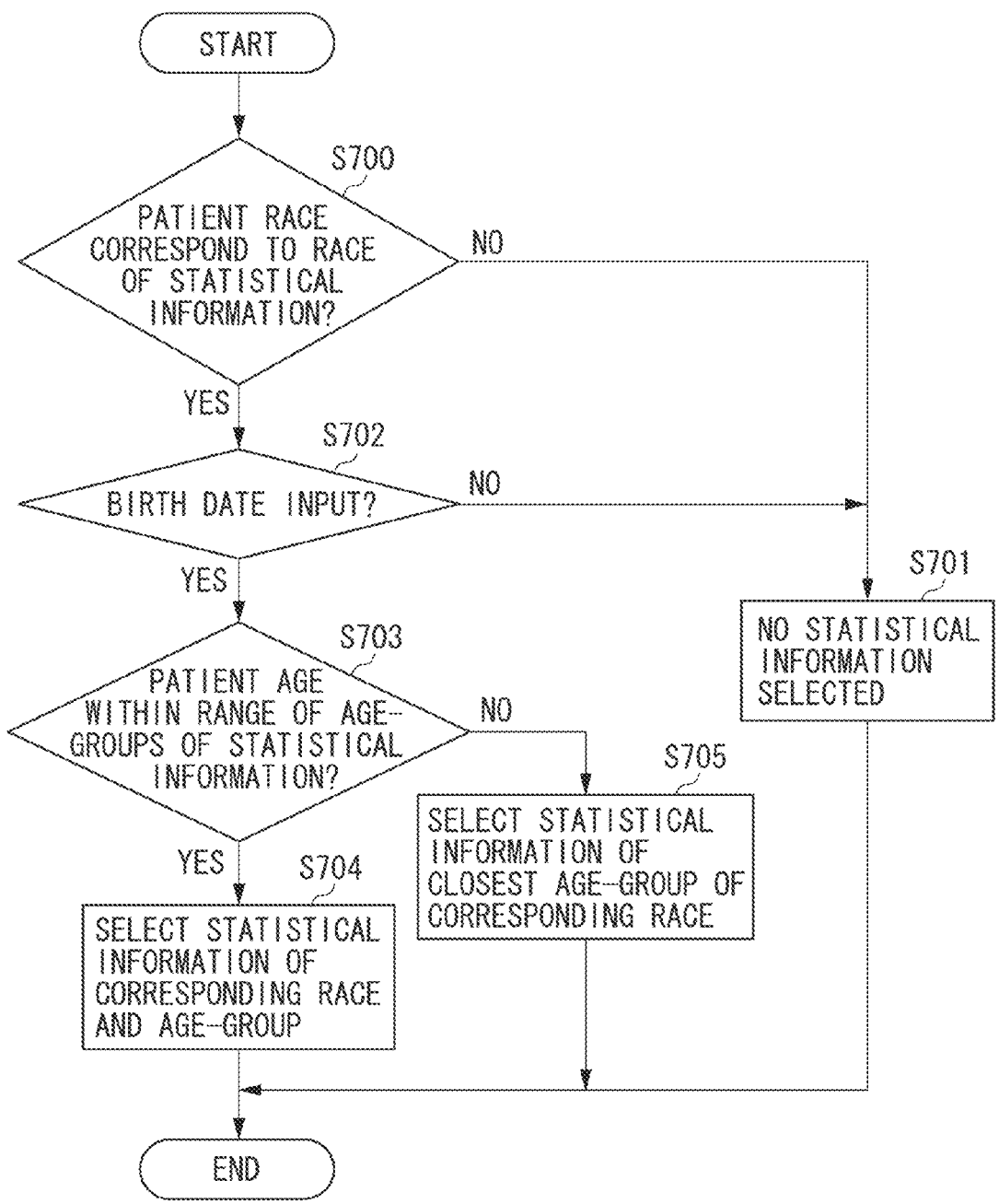
FIG. 7 is a flow chart illustrating comparison target selection according to an exemplary embodiment.

In the case where the age of the patient is outside the range of the age-groups of the statistical information, statistical information in the closest age-group may be selected from other races instead of from the corresponding race in step S705 illustrated in FIG. 7. For example, in a case where the race of the patient is Asian and the age of the patient is 90, since the age of the patient is closer to the age-group 71-85 of statistical information B-6 of the race "White" than the age-group 61-70 of statistical information D-5 of the race "Asian" in the normal database illustrated in FIG. 6, the statistical information B-6 may be selected.

<Comparison Result Generation and Comparison Result Display>

When an SLO fundus image, a layer thickness graph, a time series variation graph, measured values such as the Cup and the Disc, is displayed, a result of a comparison with the statistical information selected by the comparison target selection is generated and displayed.

Figure 10:
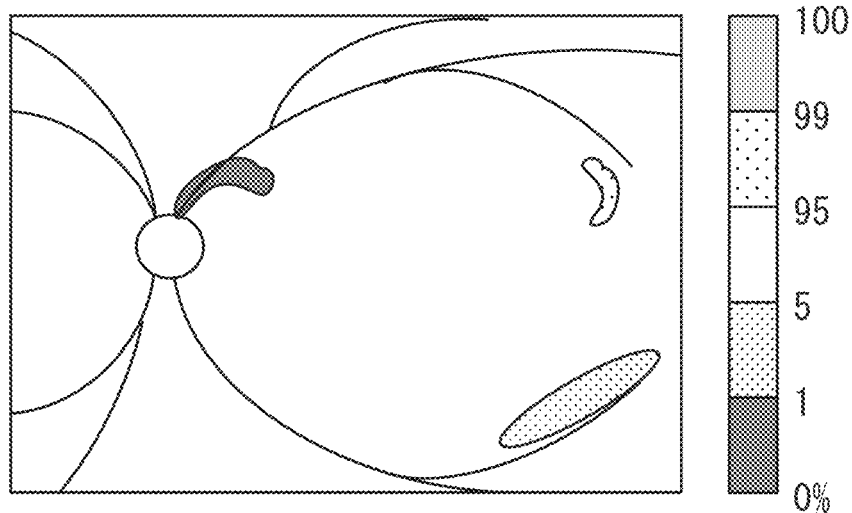
FIG. 10 illustrates an example of a displayed result of a comparison of an SLO image with statistical information in a normal database.
Figure 11:
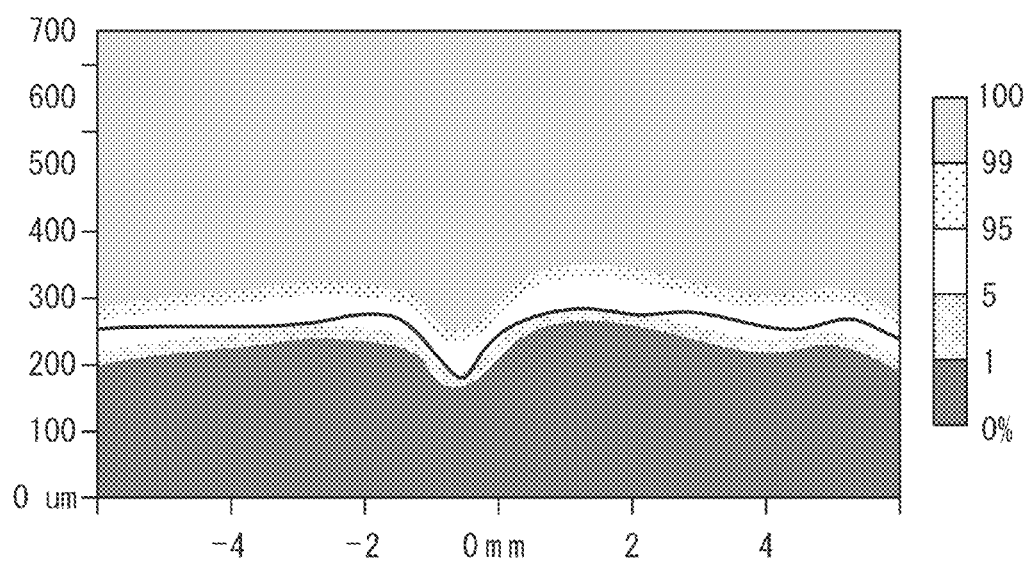
FIG. 11 illustrates an example of a displayed result of a comparison of a layer thickness graph with statistical information in a normal database.
Figure 12:
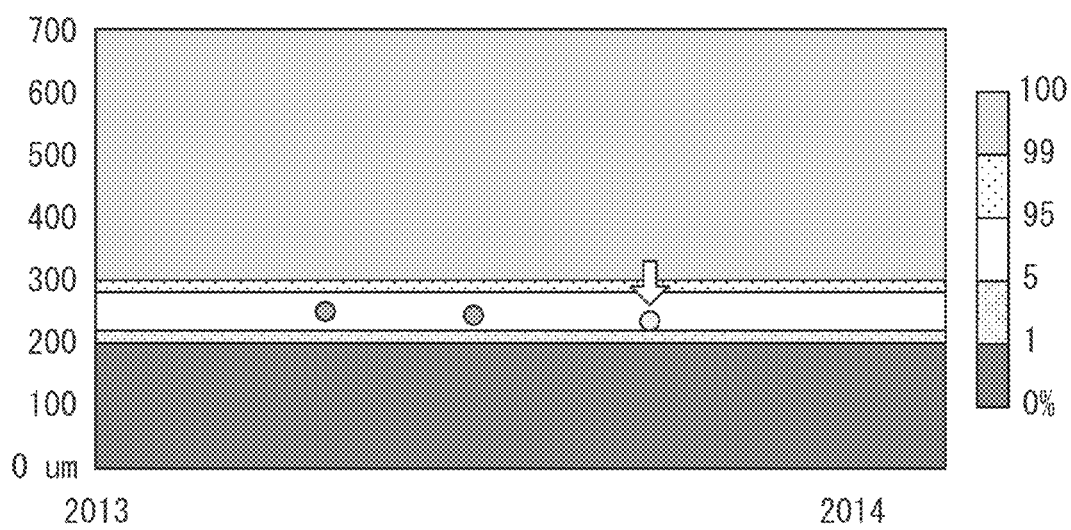
FIG. 12 illustrates an example of a displayed result of a comparison of a time series variation graph with statistical information in a normal database.

FIGS. 10, 11, and 12 illustrate display examples of results of comparisons with an SLO fundus image, a layer thickness graph, and a time series variation graph, respectively, for macular disease analysis. For macular disease analysis, results of comparisons with the statistical information in the normal database are classified into five ranges including 99-100%, which is a range outside an upper limit of a normal value range, 95-990, which is a range of an upper borderline, 5-95%, which is the normal value range, 1-5%, which is a range of a lower borderline, and 0-1%, which is a range outside a lower limit of the normal value range. With indexes of the respective categories, the results of comparisons are superimposed on the SLO image and displayed in different colors corresponding to the categories. The transmittance of each superimposed color may be changed.

For glaucoma analysis, results of comparisons are classified into ranges including 5-100%, which is a range including a normal value range and a range outside an upper limit of the normal value range, 1-5%, which is a range of a lower limit borderline, and 0-1%, which is a range outside a lower limit of the normal value range, and displayed in different colors corresponding to the categories (not illustrated).

FIG. 13 illustrates a display example of a result of a comparison with measured values such as the Cup and the Disc. For the Cup and the Disc, results of comparisons are classified into ranges including 99-100%, which is a range outside an upper limit of a normal value range, 95-99%, which is a range of an upper limit borderline, 5-950, which is the normal value range, and 0-5%, which is a range outside a lower limit of the normal value range, and backgrounds of cells displaying the measured values are displayed in different colors corresponding to the categories. In this example, the value "C/D Horizontal" of the left eye is displayed in a color corresponding to the range 95-99%, which is the range of the upper limit borderline, and the rest are displayed in a color corresponding to the range 5-95%, which is the normal value range.

Figure 14:
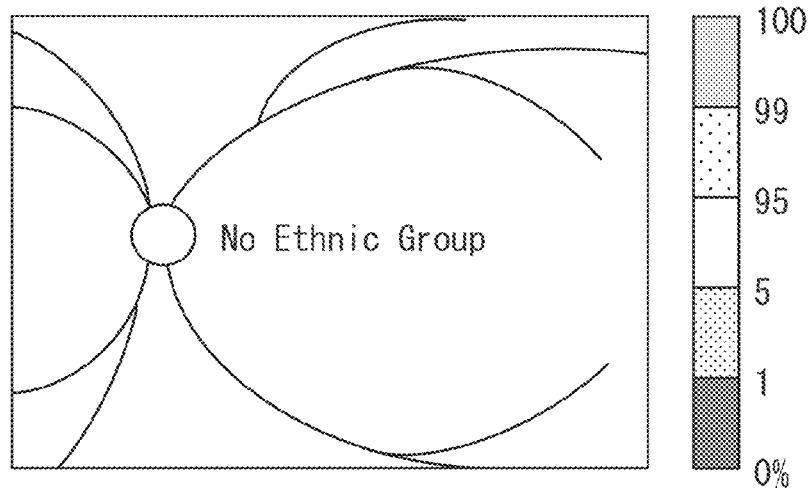
FIG. 14 illustrates an example of a displayed result of a comparison of an SLO image to statistical information in a normal database in a case where no race is input.

In a case where no statistical information is selected because the race of the patient is determined in the comparison target selection as not being input, it is not possible to display a comparison result. Thus, for example as illustrated in FIG. 14, an indication that the race is not input is superimposed on the SLO fundus image. In this example, the text "No Ethnic Group" is superimposed.

Figure 15:
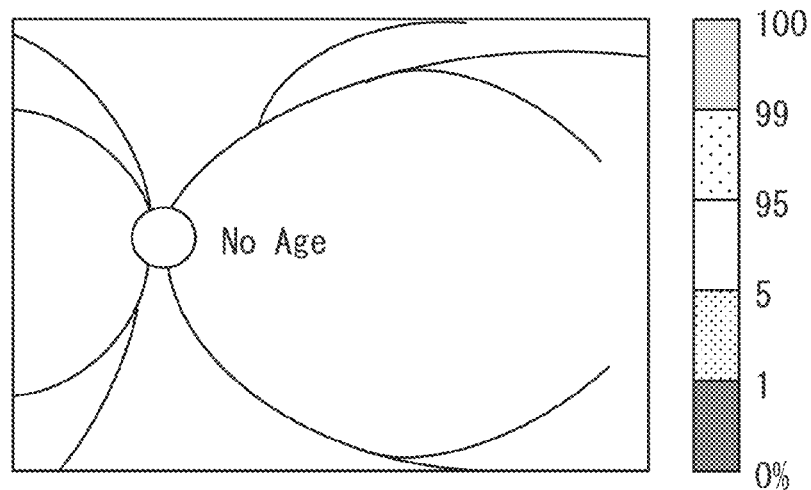
FIG. 15 illustrates an example of a displayed result of a comparison of an SLO image with statistical information in a normal database in a case where no birth date is input.

In a case where no statistical information is selected because the birth date of the patient is determined in the comparison target selection as not being input, it is not possible to display a comparison result. Thus, for example as illustrated in FIG. 15, an indication that the age of the patient is unknown because the birth date is not input is superimposed on the SLO fundus image. In this example, the text "No Age" is superimposed.

In a case where the race of the patient is not input and the default race is compared and determined to correspond thereto in the comparison target selection, an indication that the default race is compared is displayed. For example, if the race is normally displayed as illustrated in FIG. 16 at the time of inputting a race, parentheses are added as illustrated in FIG. 17. Alternatively, characters or backgrounds may be displayed in different colors.

Figure 18:
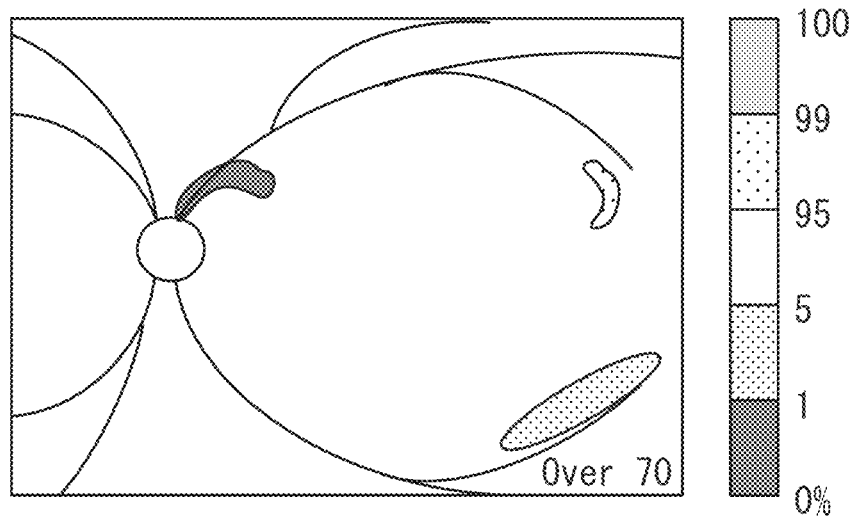
FIG. 18 illustrates an example of a displayed result of a comparison of an SLO image with statistical information in a normal database in a case where an age of a patient is outside a range of age-groups of the statistical information.
Figure 19:
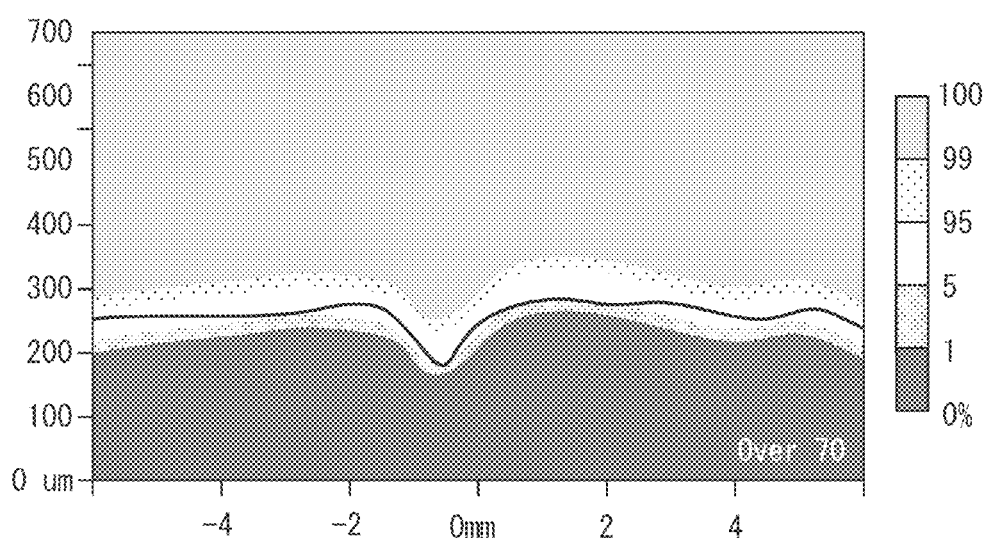
FIG. 19 illustrates an example of a displayed result of a comparison of a layer thickness graph with statistical information in a normal database in a case where an age of a patient is outside a range of age-groups of the statistical information.
Figure 20:
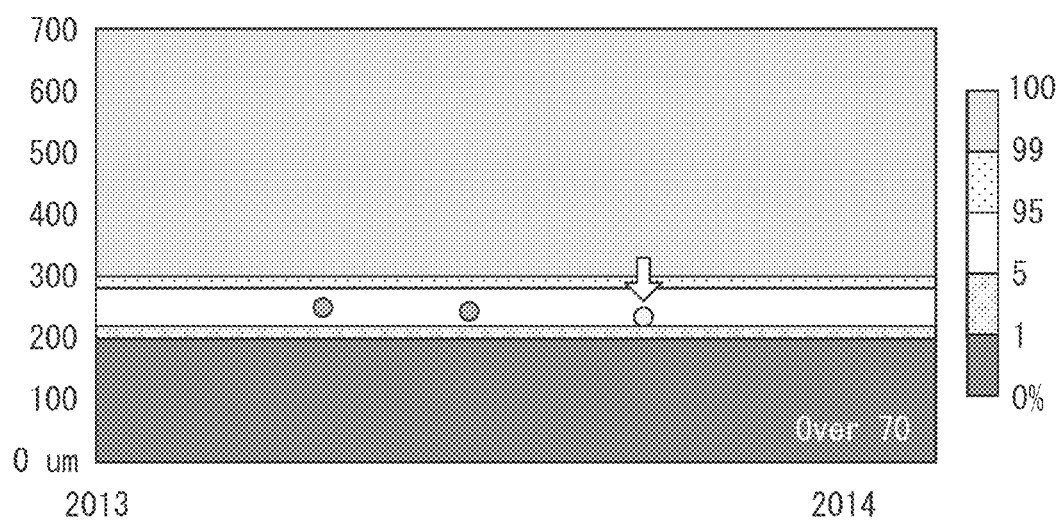
FIG. 20 illustrates an example of a displayed result of a comparison of a time series variation graph with statistical information in a normal database in a case where an age of a patient is outside a range of age-groups of the statistical information.

In a case where the age of the patient is determined as being outside the range of the age-groups of the statistical information and the statistical information in the closest age-group is selected in the comparison target selection, an indication that a comparison is made to the statistical information in the closest age-group is displayed as illustrated in FIGS. 18, 19, and 20. In these examples, in a case where the race of the patient is Asian and the age of the patient is 75, since the age of the patient is higher than the age-group 61-70, which is the closest age-group in the normal database illustrated in FIG. 6, "Over 70" is displayed. In a case where the race of the patient is Asian and the age of the patient is 15, the age of the patient is lower than the age-group 18-30, which is the closest age-group in the normal database illustrated in FIG. 6, "Under 18" is displayed (not illustrated).

In a case where the age of the patient is outside the range of the age-groups of the statistical information in the corresponding race, as the age difference from the closest age-group is smaller, the credibility of the comparison result becomes higher. On the other hand, as the age difference is larger, the credibility of the comparison result becomes lower. Thus, the color of the indication that the comparison is made to the statistical information in the closest age-group may be changed according to the age difference from the closest age-group. For example, the indication is displayed in blue if the age difference is smaller than 10, yellow if the age difference is 10 to 20, or red if the age difference is not smaller than 30.

In a case where the age of the patient is outside the range of the age-groups of the statistical information in the corresponding race, if statistical information in the closest age-group is selected not from the corresponding race but from other races in the comparison target selection, an indication thereof is displayed (not illustrated). For example, in a case where the race of the patient is Asian and the age of the patient is 90, if statistical information B-6 of the race "White", the age-group of which is closer to the age of the patient than the age-group 61-70 of statistical information D-5 of the race "Asian", is selected instead of the statistical information D-5 in the normal database illustrated in FIG. 6, "White: Over 85" or the like is displayed.

Figure 21:
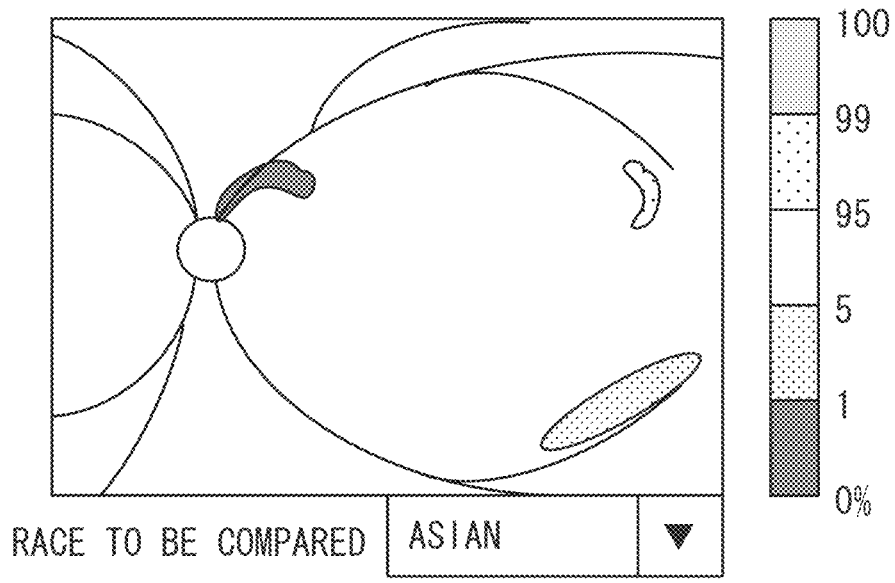
FIG. 21 illustrates an example in which a plurality of comparison target races is selected and displayed.

In a case where a plurality of races of the statistical information are selected as comparison targets in the comparison target selection, a comparison result is generated for each of the selected races of the statistical information. As illustrated in FIG. 21, the race of the comparison target is selected to change the race of the comparison target to be displayed. In a case where the races of the patient and parents of the patient are selected as the plurality of races of the statistical information, the display unit may preferentially and initially display the race of the patient. Further, in a case where a plurality of races of the statistical information is selected, the display unit may preferentially and initially display the result of the comparison with the race in which a percentage of values outside the normal value range is higher. When the race of the comparison target is changed, displays of the SLO fundus image, the layer thickness graph, the time series variation graph, and the like may automatically be changed.

As described above, even if data of a patient is outside a range of age-groups of the corresponding race of statistical information in the normal database, the data can be compared with the statistical information in the normal database. This increases diagnostic efficiency. Furthermore, even if an input race is different from the races of the statistical information in the normal database, the data can be compared with the statistical information in the normal database. This increases diagnostic efficiency.

Other Embodiments

Additional embodiments can also be realized by a computer of a system or apparatus that reads out and executes computer executable instructions recorded on a storage medium (e.g., computer-readable storage medium) to perform the functions of one or more of the above-described embodiment(s), and by a method performed by the computer of the system or apparatus by, for example, reading out and executing the computer executable instructions from the storage medium to perform the functions of one or more of the above-described embodiment(s). The computer may comprise one or more of a central processing unit (CPU), micro processing unit (MPU), or other circuitry, and may include a network of separate computers or separate computer processors. The computer executable instructions may be provided to the computer, for example, from a network or the storage medium. The storage medium may include, for example, one or more of a hard disk, a random-access memory (RAM), a read only memory (ROM), a storage of distributed computing systems, an optical disk (such as a compact disc (CD), digital versatile disc (DVD), or Blu-ray Disc (BD)™), a flash memory device, a memory card, and the like.

While the present disclosure has been described with reference to exemplary embodiments, it is to be understood that these exemplary embodiments are not seen to be limiting. The scope of the following claims is to be accorded the broadest interpretation so as to encompass all such modifications and equivalent structures and functions.

This application claims the benefit of Japanese Patent Application No. 2013-221089 filed Oct. 24, 2013, which is hereby incorporated by reference herein in its entirety.

What is claimed is:

1. An ophthalmologic system comprising:
    an analyzing unit configured to analyze a tomographic image of an eye of a patient;
    a patient information acquiring unit configured to acquire a race of the patient as patient information;
    a default race setting unit configured to set a race to be used in a case where no race is acquired by the patient information acquiring unit;
    a statistical information storage unit configured to store statistical information created for each race;
    a comparison target selecting unit configured to select statistical information, based on the race acquired by the patient information acquiring unit, from the statistical information storage unit in a case where the race is acquired by the patient information acquiring unit and to select statistical information, based on the race set by the default race setting unit, from the statistical information storage unit in a case where no race is acquired by the patient information acquiring unit; and
    a comparison unit configured to compare a result of the analysis performed by the analyzing unit with the statistical information selected by the comparison target selecting unit.

2. The ophthalmologic system according to claim 1, further comprising a display unit configured to display a result of the comparison performed by the comparison unit.

3. The ophthalmologic system according to claim 2, wherein the store statistical information is created from imaging data of a plurality of healthy eyes.

4. The ophthalmologic system according to claim 1, wherein the store statistical information is created from imaging data of a plurality of healthy eyes.

5. The ophthalmologic system according to claim 1, further comprising a display unit configured to display a result of the comparison performed by the comparison unit, wherein in a case where no statistical information is selected by the comparison target selecting unit because no race is acquired, the display unit displays an indication that represents the comparison cannot be performed because the race is unknown.

6. The ophthalmologic system according to claim 1, further comprising a display unit configured to display an indication that represents the statistical information is selected based on the race set by the default race setting unit.

7. The ophthalmologic system according to claim 1,
    wherein the patient information acquiring unit acquires race of the patient, parents of the patient, and grandparents of the patient as the patient information, and
    wherein the comparison target selecting unit selects the statistical information based on not only the race of the patient but also the race of the parents and/or the grandparents.

8. The ophthalmologic apparatus system according to claim 7, wherein the comparison unit performs the comparison with the statistical information for the plurality of races selected by the comparison target selecting unit, wherein the ophthalmologic apparatus further comprises a display unit configured to display a result of the comparison performed by the comparison unit, wherein the display unit is capable of switching and displaying the results of the comparison with the statistical information for the plurality of races, and wherein the display unit preferentially displays the result of the comparison with the statistical information for the race of the patient over the results of the comparison with the statistical information for the races of the parents and/or the grandparents.

9. The ophthalmologic system according to claim 7, wherein the comparison unit performs the comparison with the statistical information for the plurality of races selected by the comparison target selecting unit, wherein the ophthalmologic apparatus further comprises a display unit configured to display a result of the comparison performed by the comparison unit, and wherein the display unit is capable of switching and displaying the results of the comparison with the statistical information for the plurality of races.

10. The ophthalmologic system according to claim 9, wherein the display unit displays the result of the comparison with the race in which a percentage of values outside a normal value range is higher.

11. The ophthalmologic system according to claim 1, further comprising a display unit configured to display an indication that represents no race is acquired in a case where no race is acquired by the patient information acquiring unit.

12. The ophthalmologic system according to claim 1, wherein the statistical information and the result of the analysis include layer thickness of the eye respectively.

* * * * *